United States Patent
Lupton

(10) Patent No.: US 9,446,219 B2
(45) Date of Patent: Sep. 20, 2016

(54) MULTICONDUCTOR OR MULTIPOLAR GUIDEWIRE

(71) Applicant: LAKE REGION MANUFACTURING, Chaska, MN (US)

(72) Inventor: Henry W. Lupton, Oranmore (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 0 days.

(21) Appl. No.: 14/348,689

(22) PCT Filed: Oct. 4, 2012

(86) PCT No.: PCT/US2012/058671
§ 371 (c)(1),
(2) Date: Mar. 31, 2014

(87) PCT Pub. No.: WO2013/052611
PCT Pub. Date: Apr. 11, 2013

(65) Prior Publication Data
US 2014/0236126 A1 Aug. 21, 2014

Related U.S. Application Data

(60) Provisional application No. 61/542,944, filed on Oct. 4, 2011.

(51) Int. Cl.
*A61B 5/00* (2006.01)
*A61M 25/09* (2006.01)

(52) U.S. Cl.
CPC .... *A61M 25/09* (2013.01); *A61M 2025/09133* (2013.01); *A61M 2205/00* (2013.01)

(58) Field of Classification Search
CPC .................. A61M 25/09; A61M 2025/09133; A61M 2025/09191
See application file for complete search history.

(56) References Cited

U.S. PATENT DOCUMENTS

| 5,549,109 A | 8/1996 | Samson et al. |
| 5,931,819 A * | 8/1999 | Fariabi .............. A61M 25/0158 604/525 |
| 6,141,576 A | 10/2000 | Littmann et al. |

(Continued)

FOREIGN PATENT DOCUMENTS

| EP | 0419277 A1 | 9/1990 |
| WO | WO 00/62851 | 10/2000 |
| WO | WO2007054325 A1 | 5/2007 |

OTHER PUBLICATIONS

International Search Report for PCT/US2012/058671 dated Jan. 28, 2013, 2 pages.

*Primary Examiner* — Max Hindenburg
(74) *Attorney, Agent, or Firm* — Grady J. Frenchick; Michael F. Scalise

(57) ABSTRACT

This invention is a multipolar or multi-conductor guidewire which can be navigated or steered through the vasculature from outside a patient's body to perform a medical procedure within the patient's vasculature. In one embodiment, a guidewire of this invention has at least 4, preferably at least 6, to as many as 10 or more distal-to-proximal conductive pathways, which are substantially longitudinally parallel to each other running linearly along substantially the majority if not the entire length of the guidewire body, preferably in a printed circuit format. In a further practice, the conductive pathways helically wound around the guidewire body.

21 Claims, 2 Drawing Sheets

(56) References Cited

U.S. PATENT DOCUMENTS

| | | |
|---|---|---|
| 6,973,352 B1 | 12/2005 | Tsutsui et al. |
| 7,627,382 B2 | 12/2009 | Minar et al. |
| 7,822,464 B2 * | 10/2010 | Maschke .............. A61B 5/0066 128/899 |
| 7,881,806 B2 | 2/2011 | Horrigan et al. |
| 7,883,474 B1 | 2/2011 | Mirigian et al. |
| 8,712,496 B2 * | 4/2014 | Langer .......................... 600/380 |
| 2009/0112128 A1 | 4/2009 | Schiff et al. |
| 2009/0131925 A1 | 5/2009 | Tempel et al. |

* cited by examiner

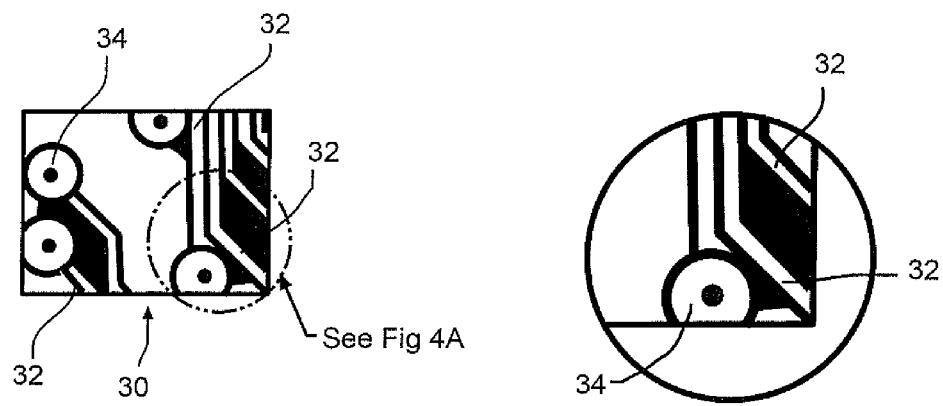
FIG. 4
FIG. 4A
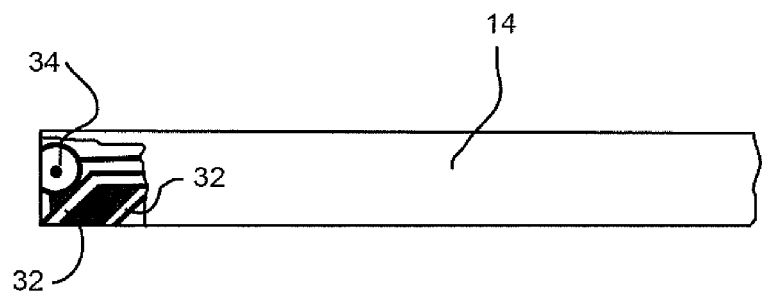
FIG. 5

MULTICONDUCTOR OR MULTIPOLAR GUIDEWIRE

This invention relates to medical guidewires having multiple electrically conductive pathways extending from substantially their distal ends to substantially their proximal ends.

There is a need in the medical industry for a steerable, torquable (i.e., can be rotated with essentially 1:1 rotational fidelity), pushable, and flexible device capable of navigating complex vascular pathways. Further there is a perceived desire in the medical industry for a device which is capable of navigating complex vascular anatomy and which also has the capability of providing multiple electrically conductive pathways from about the proximal end of the device to approximately its distal end. These multiple conductive pathways, when coupled to specific distal and proximal subassemblies e.g., connectors and lead structures, can be used for e.g., pacing, mapping, sensing, defibrillating and to monitor or treat electrical or electrophysical phenomena within the body from outside the body. A steerable, rotatable and pushable elongate device such as a guidewire, having multiple distal to proximal electrically conductive pathways for endovascular procedures is of particular interest.

One approach that has been use is to insert multiple insulated cables or wires inside a hollow tube, e.g., a segment of hypotube. Another approach has been simply to wrap one or more insulted wires about the outside of a solid core guidewire or guidewire core. The tube does not easily perform the functions of steerability and rotatability so as to permit efficient navigation of complex vasculature. The expedient of wrapping the insulated conducting cables or wires around a solid core, while providing better vascular navigation capabilities means the overall diameter of the core structure has to be reduced to provide lumen or intravascular space to accommodate the cables and core structure in the limited lumen or sectional area available. This has the drawback or reducing corewire stiffness and overall performance.

BRIEF SUMMARY OF THE INVENTION

This invention is a multipolar or multi-conductor guidewire. A guidewire as used herein means an elongate device, e.g., 50 cm to 300 cm in length, which can be navigated or steered through the vasculature from outside a patient's body to perform a medical procedure within the patient's vasculature. In one embodiment, a guidewire of this invention has at least 4, preferably at least 6, to as many as 10 or more distal-to-proximal conductive pathways. In a preferred practice of this invention, the conductive pathways are substantially longitudinally parallel to each other running linearly along substantially the majority if not the entire length of the guidewire body. In a further practice, the conductive pathways 32 are helically wound (FIGS. 4A and 5) around the guidewire body.

In a preferred method of creating a structure of this invention the conductive pathways are "printed" onto an insulative layer such as a polymeric insulative layer which itself surrounds, coats, or otherwise envelopes and is adhered to the guidewire body. The limits of circumferential space (and any required conductor separation required to eliminate "cross-talk" or electrical interferences between the conductor pathways or shorting) determine the circumferential width e.g., in degrees, and thus the number of conductors that can be placed on a single guidewire body structure. For example, an "n" conductor guidewire would require a number of degrees of separation of about (360°/n)–(minimum number of degrees of circumferential separation to avoid electrical interference between pathways). It is also to be recognized that the core wire itself may provide an additional conductive pathway beyond the pathways disposed along its outside.

For example an electrically insulative coating, such as an insulative polymer, can be applied to e.g., the outside of a guidewire core wire or mandrel body. Conductive metallic film, e.g., gold, can then be deposited on the insulative layer. The conductive film is etched or otherwise partially removed in some fashion to leave a plurality of conductive pathways running the length of the guidewire body, preferably parallel to the axis of the guidewire. Photolithography processes are well known and could be employed in the fashion suggested to create multiple conductive pathways along a guidewire core or guidewire elongate body. The conductive pathways themselves then could be covered with a second insulative layer and another series of conductive pathways created from a second layer of conductive material. A series of conductive pathways is created in this process which then can be used to electronically couple to devices, e.g., electrodes or connectors, disposed on the distal and proximal ends of the guidewire. Monitors, stimulators, and various other electronic signal treatment, analysis, and generation devices are connected to the guidewire's proximal end generally outside the patient's body after the guidewire distal end structure is directed to or navigated to the vascular site of medical interest.

In essence multiple contacts on the distal and proximal ends of the guidewire can be created, the guidewire itself providing the properties to permit placement of those electrical contacts as appropriate to the electromedical phenomena being monitored, altered, or created. Monitoring, sensing, pacing, defibrillating, mapping, ablation, and numerous other procedures whereby electrical phenomena are affected or determined within the body will be suggested to one skilled in this art by this disclosure.

In a further approach, concentric, e.g., gold foil, conductive pathways separated by suitable insulative materials could be used, both the conductive layers and the insulative layers being concentric tubes. This approach has a potential drawback in that the sectional diameter of the guidewire structure is slightly increased by each alternating layer of insulative material and conductive material.

A typical application of this invention would be as follows: A guidewire core comprising a conductive metal is coated with or sheathed in e.g., a polyethyleneterephthalate (PET), insulative layer. Conductive metallic film is disposed upon the PET insulative layer. The metallic file may encircle the guidewire core partially or completely. If used, the metallic can be partially removed leaving electrically separated conductive pathways on the guidewire structure. Circular or partially circular conductive pathways can be used. If a completely circular pathway is used, i.e., it enshrouds the guidewire body or core wire completely (360°), then the metallic conductive material may be partially removed, e.g., by etching or completely covered with a second layer of insulative material. At the distal and proximal ends of the guidewire structure the conductive pathways can be electrically coupled, e.g., by the use of conductive epoxy, to e.g., stainless steel or platinum distal or proximal conductive electrodes and couplers. Insulative polymeric materials, e.g., PET, can be shrunk over the conductive pathways to prevent shorting within the body or electrical cross-talk.

In a further variation, polyimide tubes are used to separate the conductive pathways alone or in conjunction with PTFE coatings or sleeves.

BRIEF DESCRIPTION OF THE FIGURES

FIGS. 4 and 4A show a segment of "printed" conductors i.e., a printed circuit, according to this invention.

FIG. 5 is a perspective view of a core wire 14 supporting conductive pathways 32 and electrical contacts 34.

DETAILED DESCRIPTION OF THE INVENTION

A comparison between the present invention and prior art approaches to creating multiple conductive pathways on a steerable, rotatable or pushable elongate structure is shown in the FIGS.

Figure 1:
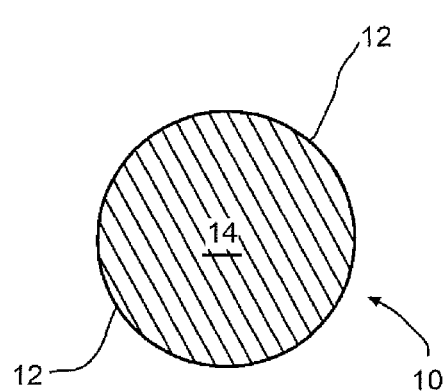
FIG. 1 shows in section a typical guidewire core wire, generally about 0.015 inches in diameter for most guidewire structures.

FIG. 1 shows in cross-section a typical guidewire core wire 10 where guidewire core wire 10 defines an outer surface 12. As is shown, core wire 10 is substantially solid in cross-section 14 having a typical diameter of 0.014".

Figure 2:
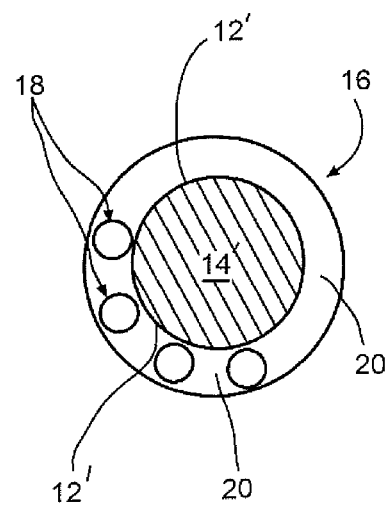
FIG. 2 shows a guidewire corewire or mandrel section having a diameter reduced from that of the core wire of FIG. 1 to permit the disposition of conductive cables or wires on the outside of the core wire. The wires or conductibles are insulated from each other by a non-conductive matrix or insulative material.

FIG. 2 shows in section a guidewire core wire 16 which is smaller in diameter than core wire 10 of FIG. 1. Core wire 16 is of a smaller diameter to provide endovascular "space" for cables/conductors 18 and insulative material or coating 20. Corewire surface 12' and solid core 14' also is shown. Reducing the diameter of the core wire to provide cross-sectional space for conductors/coatings has the drawback of changing guidewire handling characteristics e.g., reducing stiffness and hence pushability. In short some of the multi-conductor advantages provided by a guidewire are hindered.

Figure 3:
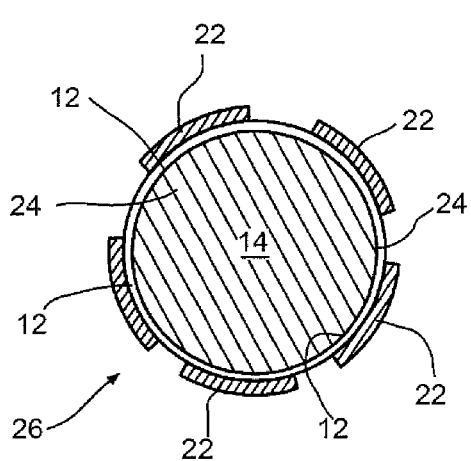
FIGS. 3 and 3A show in section an embodiment of the present invention in which conductive multiple conductors (in this case five) are disposed upon the guidewire corewire external surface in longitudinal "printed circuit" fashion.

FIG. 3 shows core wire 26 with multiple conducting pathways or tracks 22 disposed upon an electrically insulting layer 24 both being adhered to, or deposited upon, the core wire exterior surface 12. Core wire 26 could be a component of a guidewire having many other features known to one skilled in this art. Presuming solid core wire 14 is an electrically conductive material, core wire 26 of FIG. 3 could provide up to 6 proximal to distal conductive pathways 32.

FIG. 4 shows a small segment of a printed circuit 30 under moderate magnification. Pathways 22 of core wire 26 in FIG. 3 can be created in the same printed circuit manner as the circuit of FIG. 4. Pathways 32 and contacts 34 shown in FIG. 4 also can be created using printed circuit manufacturing processes on core wire 26 external surface 12.

Figure 3A:
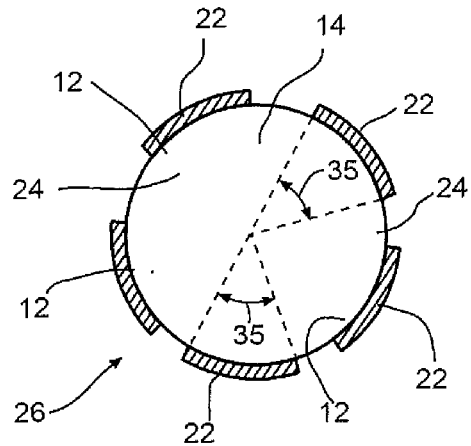

Width can be varied to increase number of conductors. In other words, as is shown in FIG. 3 fewer degrees of circumferential "real estate" or arc 35 (FIG. 3A) would be needed for each track as that diameter of the structure increases while maintaining adequate electrical continuity.

In another approach, rather than printing the conductive pathways on the guidewire, the tracks could be printed flat on a plastic sheet and the sheet formed or wrapped e.g., shrink wrapped, around the core so as to be aggressively adhered thereto.

Illustratively, a photolithography-created printed circuit segment is shown in FIG. 4.

The electrically conductive "pads" provide external access to signal originating and processing equipment. On-board (i.e., on the guidewire) signal processing and deployment e.g., by micro-processor also are contemplated.

Attached hereto and specifically incorporated herein by reference is U.S. Pat. No. 5,549,109 to Samson et al. entitled SHEATHED MULTIPOLAR CATHETER AND MULTI-POLAR GUIDEWIRE FOR SENSING CARDIAC ELECTRICAL ACTIVITY. The Samson et al. '109 patent specifically discloses guidewires with multiple electrical sensing poles or electrodes in the region of its distal end. (col. 3, line 31 et seq. and col. 4, line 55 et. seq.). That disclosure is incorporated by reference herein.

Of particular interest and specifically incorporated by reference is the discussion of Guidewire Structure starting at the end of column 8 at line 66 and continuing through column 11 line 54 of the aforementioned '109 patent. The '109 patent describes the use of multiple conductors merely twisted or wound around a guidewire core structure to form a tube of conductors (col. 9, line 29). Woven tubes of insulated conductors are also disclosed (col. 9, line 8). Numerous materials, medical procedures, and guidewire configurations which would be equally applicable to the present invention are disclosed in the '109 patent, the pertinent portions of which are incorporated by reference herein.

The following United States Patents and Patent Application Publication are also incorporated by reference herein:
U.S. Pat. No. 7,881,806 to Horrigan et al MEDICAL LEAD DELIVERY DEVICE;
U.S. Pat. No. 7,822,464 to Maschke et al. GUIDEWIRE FOR VASCULAR CATHETERS;
U.S. Pat. No. 6,973,352 to Tsutsui et al STEERABLE CARDIAC PACING AND SENSING CATHETERS AND GUIDEWIRE FOR IMPLANTING LEADS;
U.S. Pat. No. 6,141,576 to Littmann et al., INTRAVASCULAR SENSING DEVICE;
Patent Application Publication US 2009/0131925 to Tempel et al. SYSTEMS AND METHODS FOR TRANSEPTAL CARDIAC PROCEDURES, INCLUDING SEPARABLE GUIDEWIRES.

The Horrigan et al. '806 patent, incorporated by reference above discussed an elongate member 202 which also is known as a guidewire core wire.

U.S. Pat. No. 7,883,474 to Minigian et al., particularly FIG. 1 and the related disclosure, both incorporated by reference herein, shows a typical guidewire structure to which the present invention could be applied. The core wire structure shown in the '474 patent is not separately identified in the disclosure. However, structure 106 and its lead line in FIG. 1 indicate what one skilled in this art would understand to be a guidewire core wire or elongate member (as it is sometimes identified). Proximal section (102) and distal section (104) are separately delineated. One skilled in the guidewire art will readily understand and appreciate how the present invention is applied to prior art guidewire structures.

One skilled in this art will appreciate that the core wire material and the conductive pathway material need not be and often would not be the same. In fact, advantageous characteristics could be imparted to the guidewire by intentionally selecting materials which provide a desired characteristic or characteristics. For example, nitinol ribbons could be used with a stainless steel core to provide additional resilience to the composite structure.

One skilled in this art will also appreciate that the corewire material could be non-metallic, e.g., a suitable polymer such as PEEK. Were a non-metallic corewire material to be used, there would be a reduction (by 1) of the number of conductive pathways since, for example, a polymer core wire would not normally be sufficiently conductive (without some additional modification, e.g., doping) to provide an electrically conductive pathway of a conductivity approaching that of commonly used metals.

One skilled in this art will also appreciate that the selection of insulative material to be coated onto the insulatively separated pathways or tracks is of critical importance. For example, U.S. Pat. No. 7,627,382 to Minar et al., the teaching of which is incorporated by reference herein, is exemplary of both chemistry and method usable herein. Many other chemistries will occur to one skilled in this art.

It is also clear that the present invention can be adapted to many electromedical environments. Remote inputs and outputs to guidewires built according to this invention are contemplated. Signal processing, both on-board and externally, (or both) are contemplated.

What is claimed is as follows:

1. A multi-conductor guidewire, comprising:
   a) an elongate core wire having a core wire length extending from a proximal core wire end to a distal core wire end, wherein the core wire defines an exterior core wire surface having a circumference;
   b) a first insulative material supported on the exterior core wire surface;
   c) at least two electrical conductors supported on the first insulative material, wherein the electrical conductors extend from a proximal conductor end at or adjacent to the proximal core wire end to a distal conductor end at or adjacent to the distal core wire end;
   d) at least two couplers electrically connected to respective ones of the proximal conductor ends, wherein the couplers are configured to be electrically connected to an external electrical device;
   e) at least two electrical contacts electrically connected to respective ones of the distal conductor ends, wherein the electrical contacts are configured for contact with body tissue, and
   f) wherein the at least two electrical conductors are circumferentially separated from each other extending from their respective coupler to their respective electrical contact.

2. The guidewire according to claim 1 having at least four electrical conductors.

3. The guidewire according to claim 1 wherein at least one of the electrical conductors is a printed conductive pathway.

4. The guidewire according to claim 3 wherein the printed conductive pathway is a printed circuit.

5. The guidewire according to claim 1 wherein the at least two electrical conductors comprise an arc about the circumference of the exterior core wire surface.

6. The guidewire according to claim 1 where the at least two electrical conductors are at least partially helically wound around the core wire.

7. The guidewire according to claim 1 wherein the at least two electrical conductors are longitudinally parallel to each other for at least a portion of the core wire length.

8. The guidewire according to claim 1 wherein the core wire is electrically conductive and there are at least five electrical conductors to thereby provide the guidewire with at least six conductive pathways.

9. The guidewire according to claim 1 wherein there are ten or more electrical conductors.

10. The guidewire according to claim 1 wherein the at least two electrical conductors comprise nitinol and the core wire comprises stainless steel.

11. The guidewire according to claim 1 wherein the at least two conductors are of gold.

12. The guidewire according to claim 1 wherein a second insulative material is provided over the at least two electrical conductors.

13. A multi-conductor guidewire, comprising:
   a) an elongate core wire of a non-metallic material, the core wire having a core wire length extending from a proximal core wire end to a distal core wire end, wherein the core wire defines an exterior core wire surface having a circumference;
   b) at least two electrical conductors supported on the exterior core wire surface, wherein the electrical conductors extend from a proximal conductor end at or adjacent to the proximal core wire end to a distal conductor end at or adjacent to the distal core wire end;
   c) at least two couplers electrically connected to respective ones of the proximal conductor ends, wherein the couplers are configured to be electrically connected to an external electrical device;
   d) at least two electrical contacts electrically connected to respective ones of the distal conductor ends, wherein the electrical contacts are configured for contact with body tissue, and
   e) wherein the at least two electrical conductors are circumferentially separated from each other extending from their respective coupler to their respective electrical contact.

14. The guidewire according to claim 13 wherein at least one of the electrical conductors is a printed conductive pathway.

15. The guidewire according to claim 13 wherein the at least two electrical conductors comprise an arc about the circumference of the exterior core wire surface.

16. A multi-conductor guidewire, comprising:
   a) an elongate core wire having a core wire length extending from a proximal core wire end to a distal core wire end, wherein the core wire defines an exterior core wire surface having a circumference;
   b) a first insulative material supported on the exterior core wire surface;
   c) at least two electrical conductors supported on the first insulative material, wherein the electrical conductors extend from a proximal conductor end at or adjacent to the proximal core wire end to a distal conductor end at or adjacent to the distal core wire end;
   d) at least two couplers electrically connected to respective ones of the proximal conductor ends, wherein the couplers are configured to be electrically connected to an external electrical device;
   e) at least two electrical contacts electrically connected to respective ones of the distal conductor ends, wherein the electrical contacts are configured for contact with body tissue, and
   f) wherein the at least two electrical conductors are circumferentially separated from each other extending from their respective coupler to their respective electrical contact, and
   g) wherein the at least two electrical conductors comprise printed conductive pathways that are longitudinally parallel to each other for at least a portion of the core wire length.

17. The guidewire according to claim 16 wherein a second insulative material is provided over the at least two electrical conductors.

18. A multi-conductor guidewire, comprising:
   a) an elongate core wire having a core wire length extending from a proximal core wire end to a distal core wire end, wherein the core wire defines an exterior core wire surface having a circumference;
   b) an first insulative material supported on the exterior core wire surface;
   c) at least two first electrical conductors supported on the first insulative material, wherein the first electrical conductors extend from a first proximal conductor end at or adjacent to the proximal core wire end to a first distal conductor end at or adjacent to the distal core wire end;
   d) a second insulative material supported on the at least two first electrical conductors;
   e) at least two second electrical conductors supported on the second insulative material, wherein the two second electrical conductors extend from a second proximal conductor end at or adjacent to the proximal core wire end to a second distal conductor end at or adjacent to the distal core wire end;
   f) at least two first couplers electrically connected to respective ones of the two first proximal conductor ends, and at least two second couplers electrically connected to respective ones of the two second proximal conductor ends, wherein the first and second couplers are configured to be electrically connected to an external electrical device;
   g) at least two first electrical contacts electrically connected to respective ones of the two first distal conductor ends, and at least two second electrical contacts electrically connected to respective ones of the two second distal conductor ends, wherein the first and second electrical contacts are configured for contact with body tissue, and
   h) wherein the at least two first electrical conductors are circumferentially separated from each other extending from their respective coupler to their respective electrical contact, and the at least two second electrical conductors are circumferentially separated from each other extending from their respective coupler to their respective electrical contact.

19. The guidewire according to claim 18 wherein a third insulative material is provided over the at least two second electrical conductors.

20. The guidewire according to claim 18 wherein at least one of the first and second electrical conductors is a printed conductive pathway.

21. The guidewire according to claim 18 wherein the at least two first and second electrical conductors comprise an arc about the circumference of the exterior core wire surface.

* * * * *